(12) United States Patent  
Yarden et al.

(10) Patent No.: US 7,981,046 B2
(45) Date of Patent: *Jul. 19, 2011

(54) TEMPERATURE MEASUREMENT DEVICE

(75) Inventors: Moshe Yarden, Mevaseret Zion (IL); Menashe Barak, Haifa (IL)

(73) Assignee: Medisim Ltd, Airport (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/318,683

(22) Filed: Jan. 6, 2009

(65) Prior Publication Data

US 2009/0187115 A1    Jul. 23, 2009

Related U.S. Application Data

(63) Continuation of application No. 11/597,246, filed on Sep. 10, 2007, now Pat. No. 7,479,116.

(51) Int. Cl.
  *A61B 5/00* (2006.01)
  *A61B 5/01* (2006.01)
  *G01N 25/18* (2006.01)
  *G01K 1/00* (2006.01)
  *G01K 3/00* (2006.01)
(52) U.S. Cl. .......... 600/549; 374/44; 374/100; 374/110
(58) Field of Classification Search .................. 600/549; 374/44, 100, 110
See application file for complete search history.

(56) References Cited

U.S. PATENT DOCUMENTS

| | | | |
|---|---|---|---|
| 5,050,612 A | 9/1991 | Matsumura | |
| 5,255,979 A * | 10/1993 | Ferrari | 600/549 |
| 5,645,349 A | 7/1997 | Fraden | |
| 5,816,706 A | 10/1998 | Heikkila et al. | |
| 6,220,750 B1 | 4/2001 | Palti | |
| 6,280,397 B1 | 8/2001 | Yarden et al. | |
| 7,597,668 B2 * | 10/2009 | Yarden | 600/549 |
| 2003/0173408 A1 | 9/2003 | Mosher, Jr. et al. | |

FOREIGN PATENT DOCUMENTS

| | | |
|---|---|---|
| GB | 2 131 175 | 6/1984 |
| JP | 63-58223 | 3/1988 |

OTHER PUBLICATIONS

An Office Action dated Sep. 28, 2010, which issued during the prosecution of Applicant's Japanese Patent Application No. 2007-517646.
An English Translation of Japanese Patent Application No. S61-203180 dated Aug. 29, 1986, publication No. JP 63-58223.

* cited by examiner

*Primary Examiner* — Max Hindenburg
*Assistant Examiner* — Emily M Lloyd
(74) *Attorney, Agent, or Firm* — Stein McEwen, LLP

(57) ABSTRACT

A device for non-invasive measurement of the internal temperature of a physical body or thermal resistivity, the body comprising a thermally conductive medium between an internal region with a substantially constant internal temperature and an external surface with a surface temperature. The device comprises: a patch comprising one or more contact components for attachment to the external surface and an insulating cover for substantially thermally insulating the contact component from ambient thermal conditions; a reader for acquiring one or more thermal magnitudes on the patch; a processing unit for processing the thermal magnitudes to derive the internal temperature of the internal region or the thermal resistivity of the conductive medium.

18 Claims, 11 Drawing Sheets

TEMPERATURE MEASUREMENT DEVICE

CROSS-REFERENCE TO RELATED APPLICATION

This application is a continuation of U.S. patent application Ser. No. 11/597,246, filed Sep. 10, 2007 now U.S. Pat. No. 7,479,116.

FIELD OF THE INVENTION

The present invention relates to high speed, accurate temperature measurement. More particularly it relates to a device for calculating an object's internal temperature based on measuring the object's surface temperature.

BACKGROUND OF THE INVENTION

Internal temperature of a physical object can be determined from the object's external surface temperature as measured using conduction-based devices or radiation-based devices. The object being measured is assumed to have an interior with an internal temperature in a substantially steady state and an external surface. There are many examples where it is desirable to know the internal temperature of such an object Examples: monitoring the safety level inside a tank holding hazardous chemicals, determining whether livestock are ready for insemination, or checking the temperature of a patient in a hospital.

This background section of this invention specification reviews temperature measurement solutions for the body of a human being as that is a common application of temperature measurement of an object and illustrates the prior art technology.

For conduction-based measurement, the thermometer probe must be in contact with the body the entire time during the measurement. The temperature measurement is aimed at measuring the temperature of internal body tissues, which is very close to the core body temperature. The measuring device is brought into contact with external tissues, such as the skin or more preferably, somewhat thermally insulated external tissues, such as the throat. It can take about 10 minutes for convection from the external tissue to bring the measuring device to equilibrium temperature at which the internal tissue temperature can be measured. Such a long measurement time is inconvenient for the patient.

In order to shorten measurement time, a predictive algorithm can be used. However, often this incurs a tradeoff of less accuracy for shortened measurement time.

On the other hand, infra-red (IR) radiation is a very fast method of temperature measurement. Again, the most accurate measurement is made from protected external tissues, therefore IR thermometers typically measure tympanic (eardrum) temperature.

However, such a measurement is considered invasive, which may disturb the patient. Also, there is a limitation due to the fact that ear canal is not always straight so there is no direct line of sight to the eardrum. Furthermore, when using radiation for direct skin temperature measurement, the measurement is affected by environment temperature.

A variation on conduction-measurement is a thermometer that in permanent contact with the patient's skin. This solution can result in high accuracy due to the fact that the permanently-attached thermometer has had the time to reach thermal equilibrium by the time the temperature measurement is made.

However, having the thermometer attached to the body is problematic. It is inconvenient for the patient to "carry" such a device for a long time, especially for babies.

The present invention also makes use of the principle of prolonged contact for highly-accurate conduction. However only a passive component is in contact with (worn by) the patient. The actual measurement is done either by an IR measurement device that reads the temperature from the passive conductive contact device or by suitable electronic device in the case the passive component includes heat transducers.

It has been established by an earlier invention by the present inventors, U.S. Pat. No. 6,280,397, entitled "HIGH SPEED ACCURATE TEMPERATURE MEASURING DEVICE" (2001) that heat flux emitted from a human body, i.e., from blood vessels to the skin, together with the temperature measured on the skin may be used to accurately derive the body's inner temperature. The current invention also relates to using heat-flux in temperature measurement, however the analysis is done in steady state rather than in transient state. In steady state, the heat flux is constant and all the time derivatives of the temperatures are zero. Thus, a simplified model can be used to derive the internal temperature. The current invention further differs from the earlier patent in that it reads temperatures relating to a surface in persistent contact with the surface of the measured object, thereby enabling accurate calculation of the inner body temperature.

In summary, it is a main object of the present invention to provide a means for convenient, fast, accurate internal temperature measurement.

Other objects and advantages of the present invention will become apparent after reading the present specification and reviewing the accompanying drawings.

BRIEF DESCRIPTION OF THE INVENTION

There is thus provided in accordance with a preferred embodiment of the present invention, a device for a non-invasive measurement of the internal temperature or the thermal resistivity of a physical body, the body comprising a thermally conductive medium between an internal region with a substantially constant internal temperature and an external surface with a surface temperature, the device comprising:

a patch comprising at least one contact component for attachment to the external surface and an insulating cover for substantially thermally insulating the contact component from ambient thermal conditions;

a reader for acquiring one or more thermal magnitudes on the patch;

a processing unit for processing said at least one or more thermal magnitudes to derive the internal temperature of the internal region or the thermal resistivity of the conductive medium.

Furthermore, in accordance with another preferred embodiment of the present invention, gas is provided between the insulating cover and the contact component.

Furthermore, in accordance with another preferred embodiment of the present invention, the gas is transparent to infra-red radiation.

Furthermore, in accordance with another preferred embodiment of the present invention, the gas is air.

Furthermore, in accordance with another preferred embodiment of the present invention, a vacuum is provided between the insulating cover and the contact component.

Furthermore, in accordance with another preferred embodiment of the present invention, the patch comprises at least one of a plurality of measurement locations characterized in that different measurement locations facilitate different thermal boundary conditions on the external surface.

Furthermore, in accordance with another preferred embodiment of the present invention, the patch comprises three measurement locations.

Furthermore, in accordance with another preferred embodiment of the present invention, the measurement locations are characterized as having distinct properties selected from the group of properties comprising: different thermal conductivity, different thickness, or different emissivity, thus facilitating different boundary conditions on the external surface.

Furthermore, in accordance with another preferred embodiment of the present invention, the patch comprises at least one of a plurality of measurement locations characterized in that each measurement location facilitates two or more measurement spots facilitating different thermal boundary conditions on the external surface.

Furthermore, in accordance with another preferred embodiment of the present invention, the different thermal boundary conditions are characterized as having distinct properties selected from the group of properties comprising: different thermal conductivity or different thickness.

Furthermore, in accordance with another preferred embodiment of the present invention, the measurement locations are separated by thermal insulation.

Furthermore, in accordance with another preferred embodiment of the present invention, said two or more measurement spots are separated by a distance that is substantially smaller than the distance separating adjacent measurement locations to eliminate or greatly reduce two dimensional effects.

Furthermore, in accordance with another preferred embodiment of the present invention, the patch is provided with at least one pair of thermally separated heat or temperature transducers for each measurement location, each transducer provided with leads to terminals external to the patch, which the reader can contact for reading.

Furthermore, in accordance with another preferred embodiment of the present invention, the reader is an infrared radiation radiometer.

Furthermore, in accordance with another preferred embodiment of the present invention, the insulating cover is provided with a point of access through which the radiometer can acquire one or more thermal magnitudes on the patch.

Furthermore, in accordance with another preferred embodiment of the present invention, the point of access is selected from the group comprising: a window, an opening, a diaphragm, or a shutter.

Furthermore, in accordance with another preferred embodiment of the present invention, the contact component comprises one location of substantially low thermal resistivity and substantially low emissivity, the cover has low emissivity, and wherein the cover is large enough to avoid lateral heat flux, thereby allowing at a thermal steady state the temperature on the contact component to be substantially equal to the internal temperature.

Furthermore, in accordance with another preferred embodiment of the present invention, the device further comprises a user interface for enabling a user to calibrate and operate the reader and to be informed of the calculated internal temperature.

Furthermore, in accordance with another preferred embodiment of the present invention, the patch further comprises identification information about the physical body, the reader further comprises means for reading identification information.

Furthermore, in accordance with another preferred embodiment of the present invention, the means for reading the identification information is a bar code reader.

Furthermore, in accordance with another preferred embodiment of the present invention, the patch includes patient identification information.

Furthermore, in accordance with another preferred embodiment of the present invention, the contact component is provided with adhesive material for adhering the contact component to the external surface.

Furthermore, in accordance with another preferred embodiment of the present invention, the patch is provided with at least one adhesive surface.

Furthermore, in accordance with another preferred embodiment of the present invention, the reader is provided with a data communication interface to another device for storage or further processing the data.

Furthermore, in accordance with another preferred embodiment of the present invention, the processing unit is provided with a data communication interface.

Furthermore, in accordance with another preferred embodiment of the present invention, the patch further comprises an aligner for proper alignment of the reader.

Furthermore, in accordance with another preferred embodiment of the present invention, the reader further comprises a reading end that comes into contact with the patch during reading, the reading end provided with a disposable cover.

Furthermore, in accordance with another preferred embodiment of the present invention, the reader further comprises a reading end that comes into contact with the patch during reading, the reading end provided with a disposable cover. wherein the disposable probe cover is provided with electrically conductive coating enabling electrical contact to the terminals external to the patch.

There is thus also provided in accordance with a preferred embodiment of the present invention, a method for non-invasively measuring the internal temperature or thermal resistivity of a physical body, the body comprising a thermally conductive medium between an internal region with a substantially constant internal temperature and an external surface with a surface temperature, the method comprising:
  placing a patch comprising at least one contact component and an insulating cover with the contact component in contact with the external surface and allowing the contact component to reach a thermal steady state;
  acquiring one or more thermal magnitudes on the patch using a reader;
  processing with a processing unit said at least one or more thermal magnitudes to derive the internal temperature of the internal region or the thermal resistivity of the conductive medium;

Furthermore, in accordance with another preferred embodiment of the present invention, the method comprises measuring the thermal resistivity of the physical body.

Furthermore, in accordance with another preferred embodiment of the present invention, the method further comprises:
  acquiring thermal magnitudes at a plurality of measurement locations on the patch;
  solving a set of equations relating to a plurality of measurement locations to derive the internal temperature or the thermal resistivity of the conductive medium, using the relation at each location given by $$q''_K = \left(\frac{K_{eff}}{\Delta X}\right)(Tdeep - Ts)$$

where
- $q''_K$ is the heat flux across the thermally conductive medium
- $K_{eff}$ is the effective conductivity of the thermally conductive medium
- $\Delta X$ is the thickness of the thermally conductive medium
- $T_s$ is the temperature measured on the skin surface
- $T_{deep}$ is the internal temperature Furthermore, in accordance with another preferred embodiment of the present invention, the method further comprises:
- acquiring thermal magnitudes is done at different measurement spots at each of a plurality of measurement locations on the patch,
- solving a set of equations relating to a plurality of measurement locations to derive the internal temperature or the thermal resistivity of the conductive medium, using the relation at each location given by $$q'' = \frac{Ksi}{\Delta Xsi}\underbrace{(Tsi - Tci)}_{\Delta T} = \left(\frac{K_{eff}}{\Delta X}\right)(Tdeep - Tsi)$$

where
- $q''$ is the heat flux
- $K_{si}$ is the conductivity of the contact component at spot S of the i-th location
- $\Delta Xsi$ is the thickness of the contact component at spot S of the i-th location
- $T_{si}$ is the temperature of the contact component at spot S of the I-th location
- $T_{ci}$ is the temperature of the contact component at spot C of the I-th location
- $K_{eff}$ is the effective conductivity of the thermally conductive medium
- $\Delta X$ is the e thickness of the thermally conductive medium
- $T_{deep}$ is the internal temperature Furthermore, in accordance with another preferred embodiment of the present invention, the contact component comprises one location of substantially low thermal resistivity, allowing the temperature on it at a steady state to be substantially equal to the internal temperature, and wherein the step of deriving temperature comprises taking the internal temperature to be substantially equal to the external temperature.

Furthermore, in accordance with another preferred embodiment of the present invention, deriving the internal temperature involves adding a known correction value from a predetermined calibration table.

Furthermore, in accordance with another preferred embodiment of the present invention, the method further comprises repeatedly determining heat flux at the contact component and indicating if the contact component has reached a thermal steady state when the heat flux is substantially constant.

Furthermore, in accordance with another preferred embodiment of the present invention, the method further comprises repeatedly determining the temperature at the contact component and indicating if the contact component has reached a thermal steady state when the temperature is substantially constant.

BRIEF DESCRIPTION OF THE FIGURES

The invention is described herein, by way of example only, with reference to the accompanying Figures, in which like components are designated by like reference numerals.

DETAILED DESCRIPTION OF THE INVENTION

The present invention is aimed at measuring the temperature or the thermal resistivity of an object having an internal region with a temperature that is in a substantially thermal steady state, the region being in contact with a thermally conductive medium comprising one or more layers, the medium having an external surface that is accessible for reading temperatures related to the surface.

One example is measuring the temperature of a liquid flowing through an insulated pipe, with the medium being the pipe wall and the external surface being the outside insulation of the tank. Another example (FIG. 1) is measuring the temperature of the blood vessels (Tdeep) of a patient, with the medium being layers of tissues above the blood vessels and the external surface being the skin surface (temperature Ts).

For illustrative purposes, this detailed description focuses on measurement of the temperature of the body core of a patient. Therefore, it should be borne in mind that where this description refers to "body core", "tissues", and "skin surface", these terms are representative respectively of the more generic terms "internal region with a temperature that is in a substantially thermal steady state", "medium", and "external surface".

Figure 1:
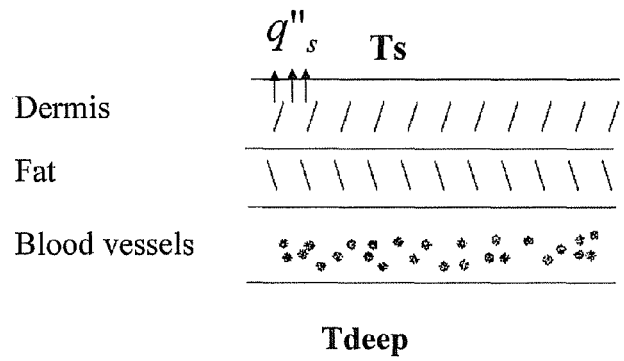
FIG. 1 illustrates heat flux $q''_s$ on the external surface of a human body.

FIG. 1 illustrates the heat flux $q''_s$ on the external surface of a body. Heat flows between the body core (Tdeep), and the external skin surface (Ts) via one or more layers of tissue. The direction of flow is from the area having the higher temperature to the one having lower the lower temperature. If it happens that the temperatures are equal, then the heat flux=0. It is assumed that the body is in a substantially in thermal steady state and that the heat flux is substantially constant.

The present invention derives Ts and $q''_s$ from temperature measurements relating to the skin surface and then determines the value of Tdeep and/or the value of the thermal resistivity of the conductive medium, defined as the relation between the effective conductivity and the thickness of the medium, by applying the one-dimensional steady state relation:

$$q''_s = \left(\frac{K_{eff}}{\Delta X}\right)(Tdeep - Ts)$$

where:
   $q''_s$ is the heat flux determined from temperatures measured at several locations on the skin surface
   Keff is the total equivalent conductivity of all layers between the skin surface and the layer of blood vessels under the surface tissues.
   $\Delta X$ is the distance from the surface to the layer of blood vessels
   $T_S$ is the temperature measured on the skin surface
As mentioned, the relation $$\left(\frac{K_{eff}}{\Delta X}\right)$$

represents the effective thermal resistivity of the conductive medium under discussion.

The present invention derives the value of Tdeep and/or the effective thermal resistivity of the conductive medium by measuring temperatures at one or more points in substantially steady thermal state on the skin surface. The points in question are located on a passive device, or patch, mounted in contact with the exterior surface of the body long enough to reach a thermal steady state.

Figure 2:
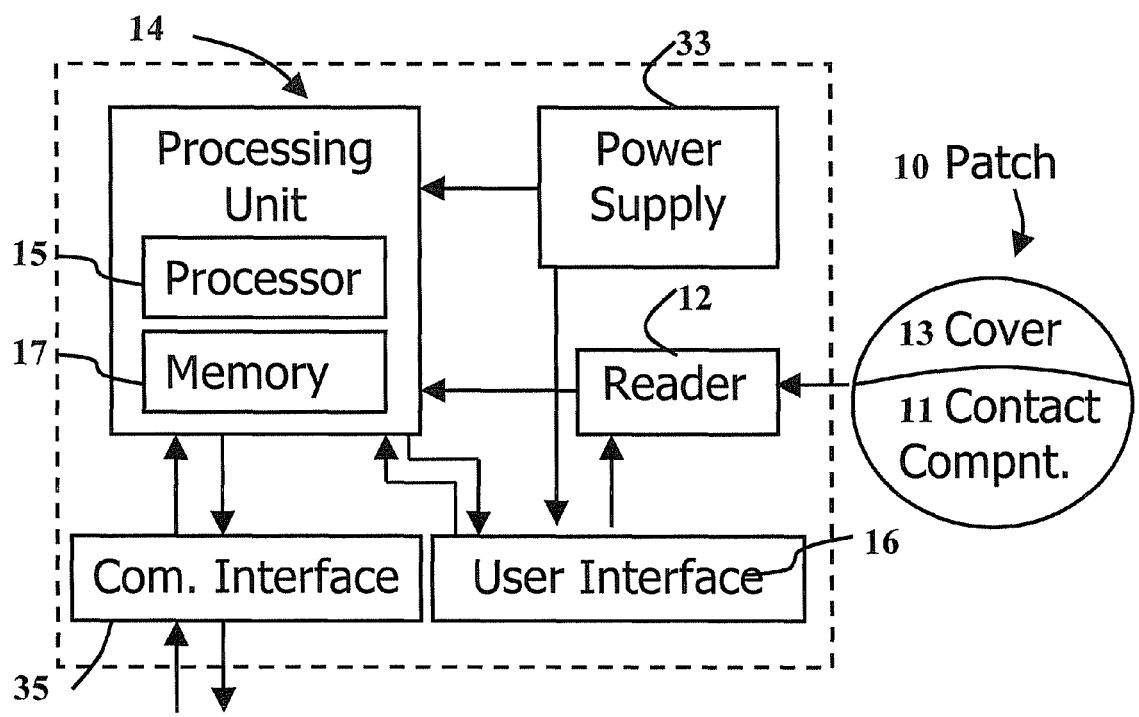
FIG. 2 is a block diagram of the present invention.
Figure 3A:
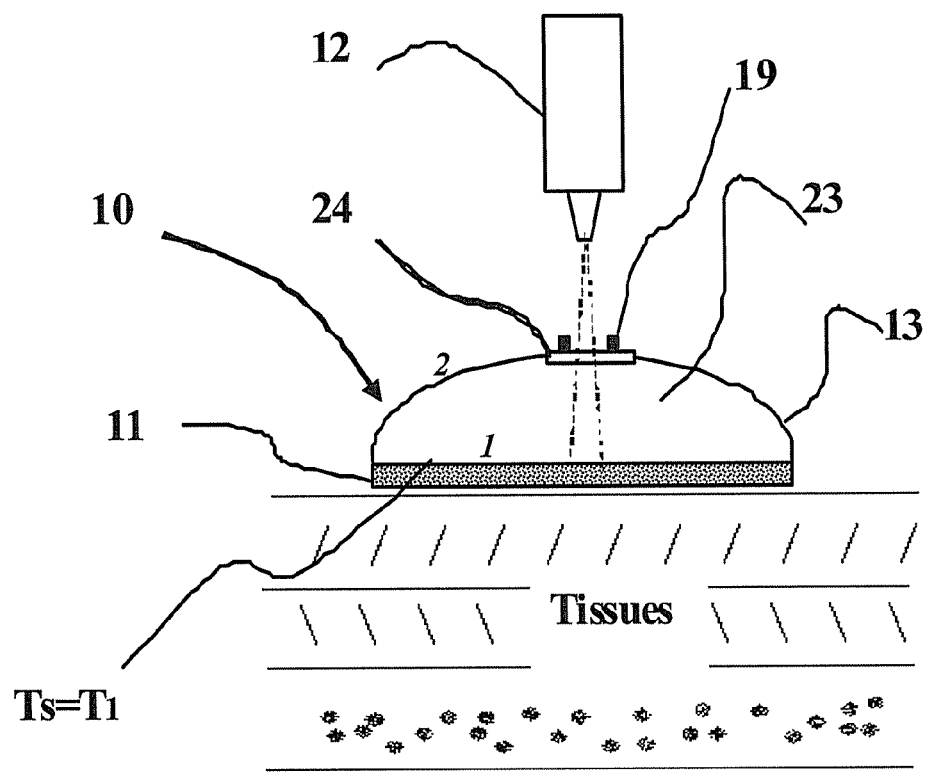
FIG. 3A is a cross section side view of a first preferred embodiment of the present invention with an infrared radiation reader.
Figure 3B:
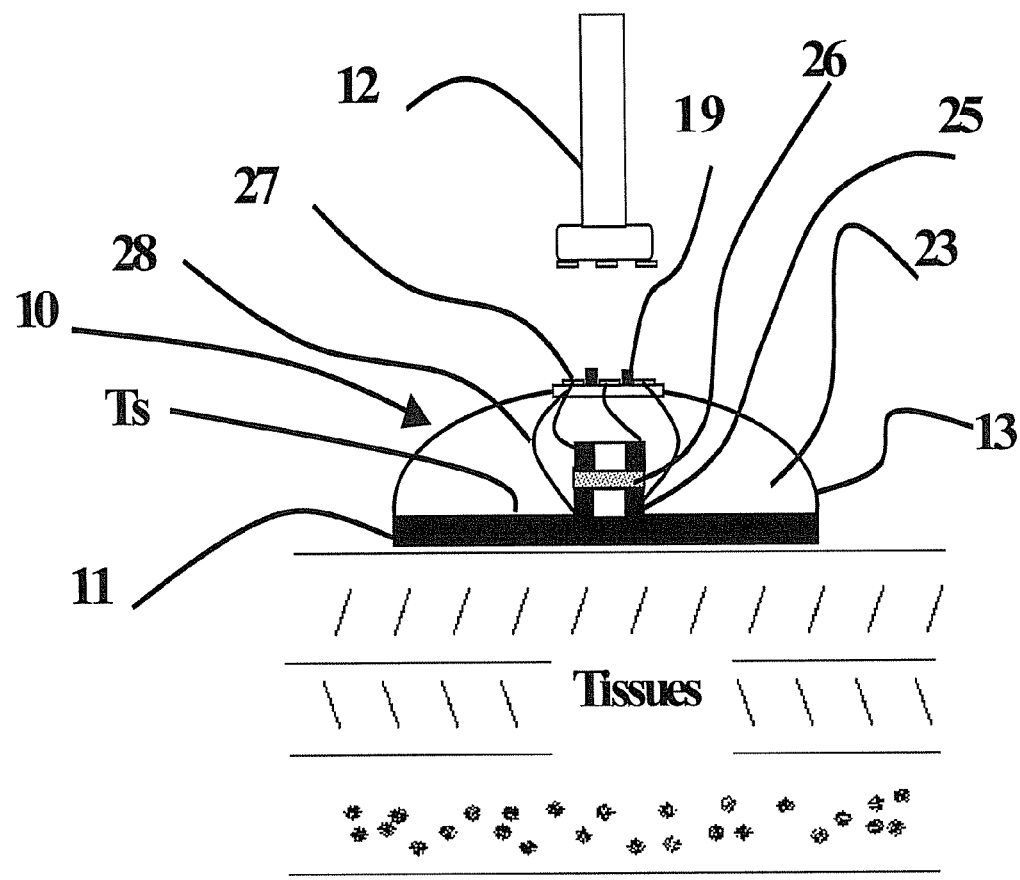
FIG. 3B is a cross section side view of a first preferred embodiment of the present invention with a thermal transducer output reader.

FIG. 2 illustrates the major elements of the present invention. The invention includes a temperature-related-magnitude reader 12, which can be implemented in several ways. FIG. 3A illustrates an implementation that reads radiated IR energy. FIG. 3B illustrates an implementation that reads electronic signals.

Patch 10 is a passive component that is attached to the patient's body. It can be attached using various well known attachment means. For example, for attachment to the body, patch 10 can comprise an adhesive on the surface in contact with the body or a strap for attachment to the body. In an industrial implementation, patch 10 could be attached to the object by a fastener, by welding, or by various other attachment means that are well know in the art.

Patch 10 comprises one or more contact components 11 in substantially thermal steadystate (thermal equilibrium) and covered by one or more covers 13. Contact component 11 is characterized by being highly conductive. Contact component 11 should be large enough to avoid two-dimensioned lateral heat flow effects perpendicular to the axis of heat flow from the internal region to the external surface. Examples of suitable material for the contact component is foil made from stainless steel or aluminum coated with a thin layer of a biocompatible coating. Cover 13 is characterized by having good insulation characteristics and being opaque to radiation. It insulates contact component 11 from ambient thermal conditions. While the term "patch" is used herein, it should be understood to refer generally to any passive component comprising a contact component 11 and cover 13 and attached to the object to be measured (for example, the patient's body).

The volume 23 defined by contact component 11 and cover 13 is characterized by being a good insulator, for example, a gas such as air, or a vacuum. Its constituent material also depends on the type of device used as a reader 12. If the reader is an IR-radiation radiometer, then the volume is also characterized by being partially or fully IR-radiation transparent. If the reader is based on other principles, such as reading electrical signals or electrical properties related to temperatures (as is described later), then the volume can be IR-opaque.

Reader 12 is used for reading thermal magnitudes related to temperatures at points on contact component 11 (and in one embodiment, on cover 13 as well). This can be done in a variety of ways.

One implementation of reader 12 is as an IR radiometer that reads the IR radiation at the points (FIG. 3A). In that case, it is necessary for cover 13, which is opaque to radiation, to include an aligner 19 for aligning reader 12 over the point and a small access point 24 in cover 13 through which radiation can pass for reading by the radiometer. One way to implement access point 24 is to make it permanently IR-transparent but small enough not to allow significant IR radiation to escape, for example as a window or opening. Another way to implement access point 24 is to make it IR-opaque but capable of being opened by radiometer reader 12 at the time of the reading, for example, as a spring-hinged shutter that is pushed open by the radiometer and closes when the radiometer is removed or as a diaphragm such as an aperture used to light entering a camera. Although it is not critical in this embodiment and in the second embodiment, how much radiation escapes through access point 24, it is preferable to minimize it for better signal to noise ratio.

Another way to implement reader 12 is as a device that derives a measurement from characteristics of electrical signals or electrical properties (FIG. 3B). In that case, points on patch 10 that are to be read are provided with a temperature transducer such as a thermistor 25 or thermocouple and the transducer output is run over leads 28 to terminals 27 on the exterior of cover 13 and to which the reader can be aligned using aligner 19 in order to read the terminal output. In order to provide the heat flux one can use two thermistors separated by insulation 26.

Processing unit 14 comprises memory 17 for data retention and comprises a processor 15 for processing the signals from reader 12 to determine the temperature at the points read and to apply algorithms to those temperatures to derive Tdeep.

User interface 16 can comprise various user interface controls, such as, display, buzzer, or control buttons, for enabling a user to operate reader 12 and be informed of processed information, in particular the value of Tdeep.

Reader 12 or processing unit 14 can also be provided with a data communication interface 35 for communication with external devices such a PC for data transfer or control. The communication can be wired or wireless, for example, a standard PC universal serial bus (USB) interface.

Power supply 33 powers active components of reader 12, processing unit 14, and user interface 16. Depending on the application the power supply could be cable to a permanent voltage source, a rechargeable battery or battery pack, or other power source.

In many implementations of the present invention, such as the medical implementation described here, it may be preferable for reasons of convenience in usage and manufacture to combine reader 12, processing unit 14, and user interface 16 into a single device.

In implementations, such as medical, where sterility is required, reader 12 may include a means for isolating reader 12 from direct contact with patch 10 to avoid cross contamination. In such a case, reader 12 further comprises a reading end that comes into contact with the patch during reading and a disposable probe cover attached over the reading end before a measurement is taken. Also, in such implementations, patch 10 is preferably implemented as a disposable adhesive patch comprising biocompatible, inexpensive materials.

Patch 10 may include an ID information means such as a bar code and reader 12 may include an ID reading means, such as a bar code reader.

Figure 4:
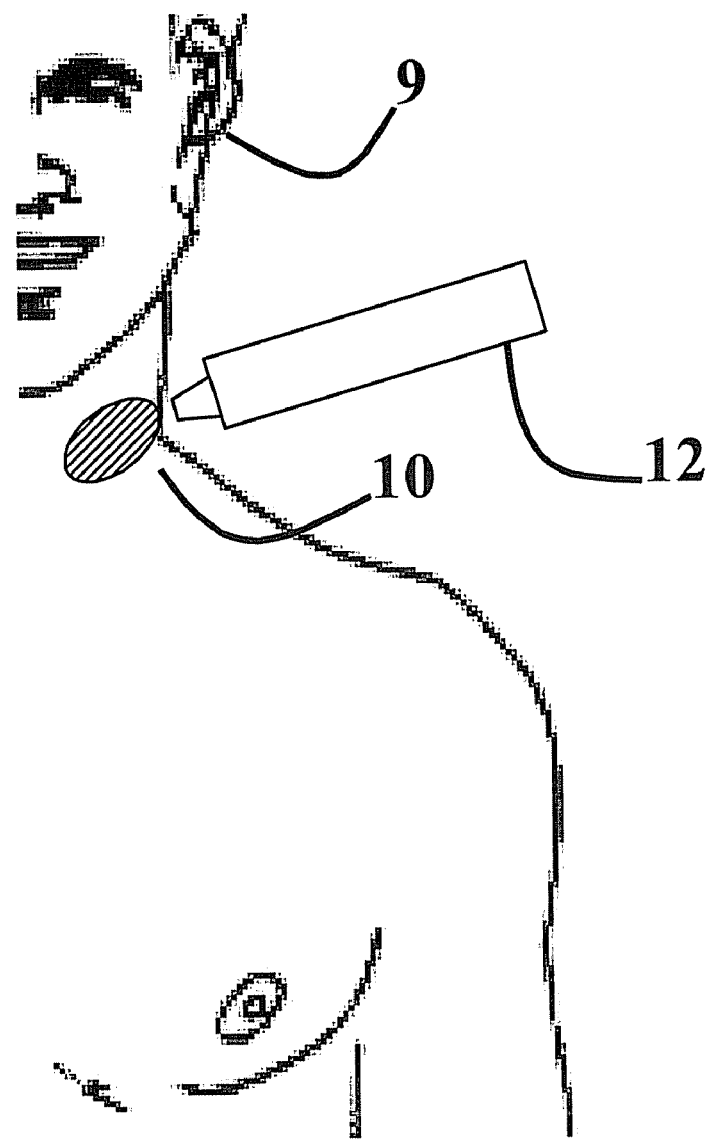
FIG. 4 illustrates a patch attached to a patient and a reader in accordance with the present invention.

FIG. 4 illustrates a patch 10 attached to a patient 9 and being read by reader 12. In this case of measuring human body temperature, patch 10 is preferably attached to the patient's skin at a point adjacent to an artery, such as the carotid artery, which has a temperature that is substantially identical to the body core temperature. As the figure shows, the present invention is noninvasive and very convenient for both the patient and the practitioner. Patch 10 can be left attached continuously to the body of the patient for an extended period, for example as an adhesive patch. Within a short period after it has been attached to the body, contact component 11 reaches a steady state after which it can be read at any time by reader 12. The reading is processed by processing unit 16 to derive the internal temperature (Tdeep) and/or the thermal resistivity, which can be communicated to a user via user interface 16, for example as a numerical representation on a set of 7-segment displays. The internal temperature as well as the patient ID could also be communicated via the communication interface to an external device such as a PC.

There are three primary preferred embodiments of the present invention. These embodiments, once understood, will suggest various equivalent implementations to one skilled in the art.

A first embodiment of the present invention is now described with reference to FIG. 3A. This embodiment requires that reader 12 be the IR radiometer implementation described earlier with reference to FIG. 3A. Therefore, in this embodiment, cover 13 of patch 10 comprises access point 24, enabling IR-radiation reading. Two readings are made, one measurement through access point 24 of IR radiation at a point, such as the one labeled 1 in the figure, on the surface of contact component 11, the other one, such as the one labeled 2 in the figure, on the external surface of cover 13. As will be explained later, for greatest accuracy, it is preferably to measure at least three pairs of such points 1 and 2, for example using a patch 10 implementation such as the one shown in FIG. 5A. In that implementation, contact component 11 is divided into three sections, AA, BB, and CC, each having a different thermal boundary condition, hence a different $q''_s$, and $T_s$. Thermal boundary conditions of points on contact component 11 can vary depending on the local features of the contact component such as thickness, its conductivity, or its emissivity. It should be noted that it is imperative to create a differentiation between the points. One can achieve it by using one or a combination of the features mentioned above.

Each section is thermally isolated from the others to eliminate lateral thermal conduction or convection between the sections. The thermal insulation can take the form of fully separate covers 13 as in FIG. 5A or dividers between sections with a common cover.

Figure 5A:
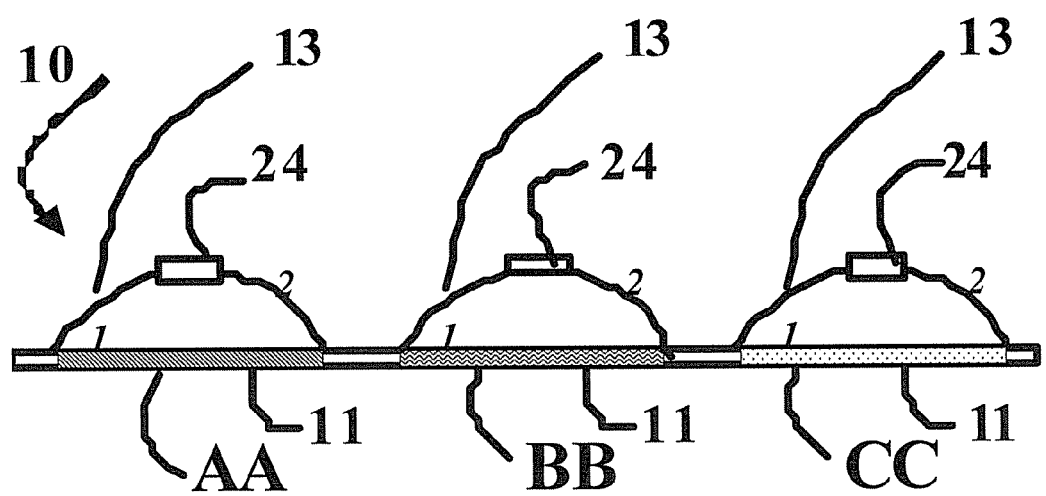
FIG. 5A is a cross section side view of a patch in accordance with a first preferred embodiment of the present invention.
Figure 5B:
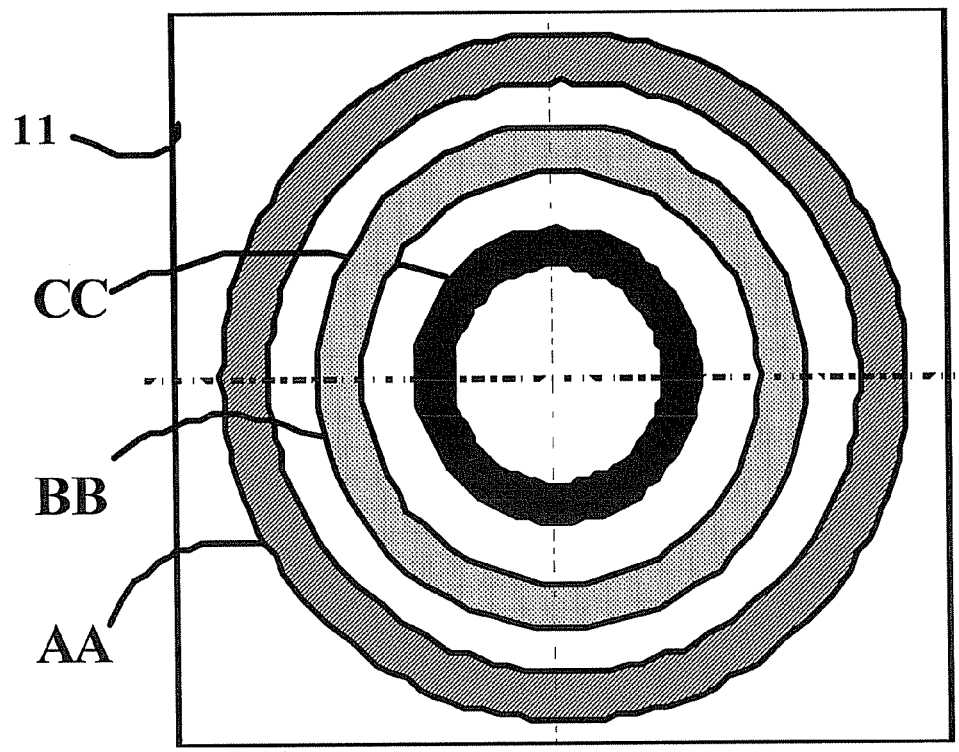
FIG. 5B is a top view of a patch implemented as concentric rings having different emissive characteristics in accordance with a first preferred embodiment of the present invention.
Figure 5C:
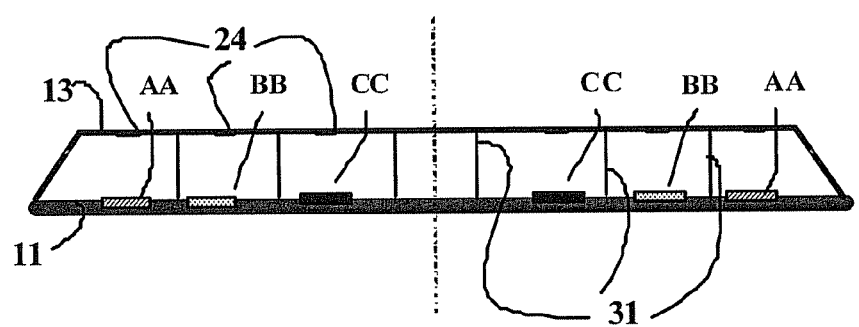
FIG. 5C is a cross section side view of a patch implemented as concentric rings having different emissive characteristics in accordance with a first preferred embodiment of the present invention.

Several other implementations of this first embodiment are now described. FIG. 5B is a top view and FIG. 5C is a side view cross section of an implementation of contact component 11 where sections AA, BB, and CC are implemented as concentric rings having different emissive characteristics and thermally isolated with dividers 31.

Figure 5D:
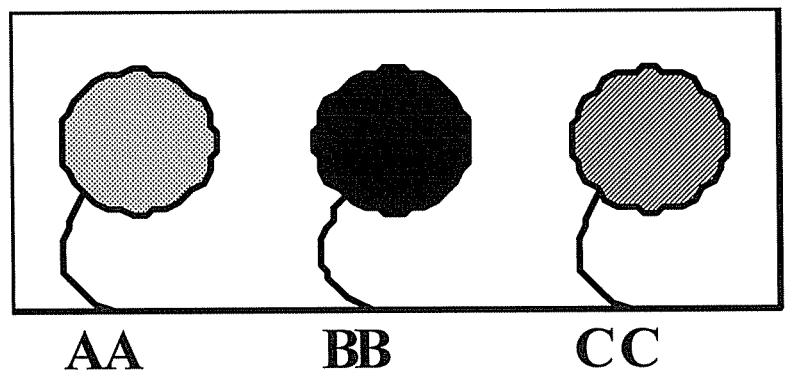
FIG. 5D is a top view of a patch implemented as adjacent circles having different emissivity, conductivity, and thicknesses in accordance with a first preferred embodiment of the present invention.
Figure 5E:
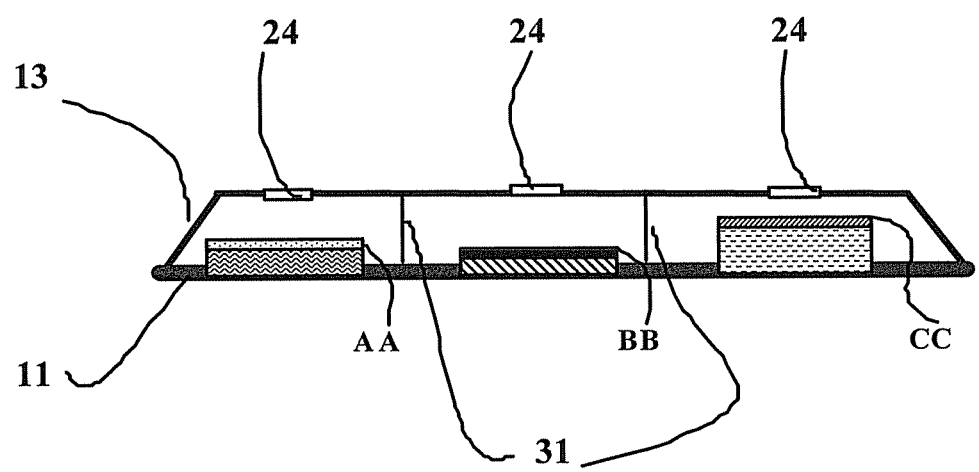
FIG. 5E is a cross section side view of a patch implemented as adjacent circles having different emissivity, conductivity, and thicknesses in accordance with a first preferred embodiment of the present invention.

FIG. 5D is a top view and FIG. 5E is a side view cross section of an implementation of contact component 11 where sections AA, BB, and CC are implemented as adjacent circles having different emissivity, conductivity, and thicknesses.

Figure 5F:
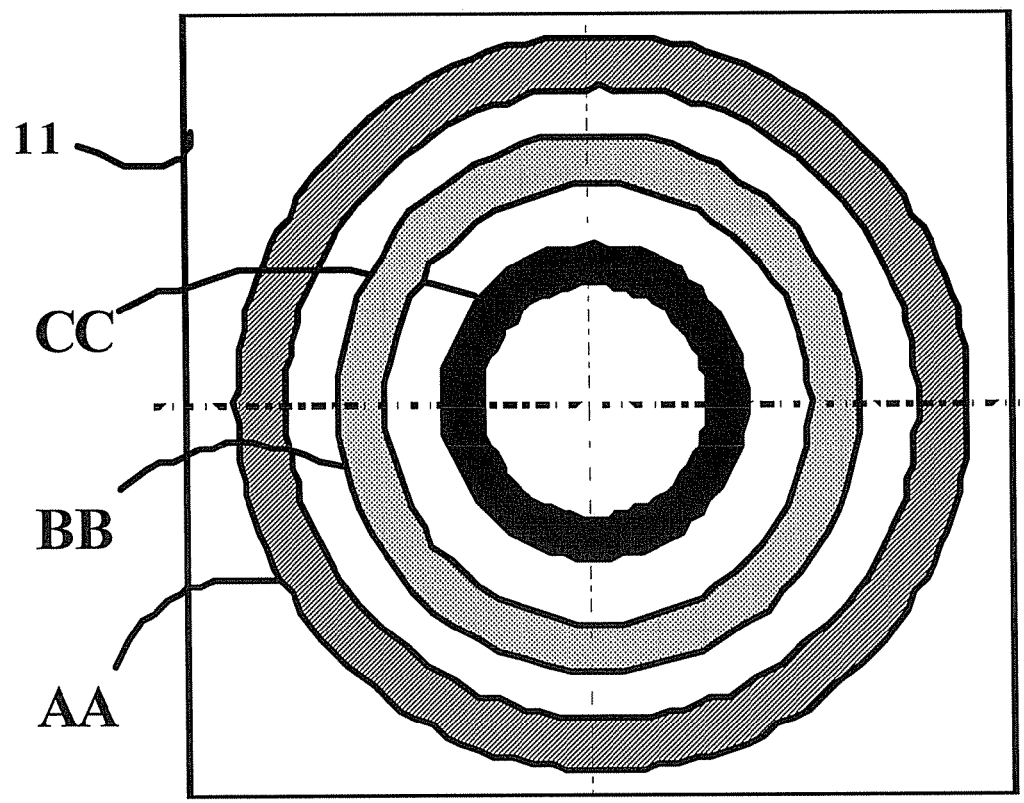
FIG. 5F is a top view of a patch implemented as concentric rings having different emissivity, conductivity, and thicknesses in accordance with a first preferred embodiment of the present invention.
Figure 5G:
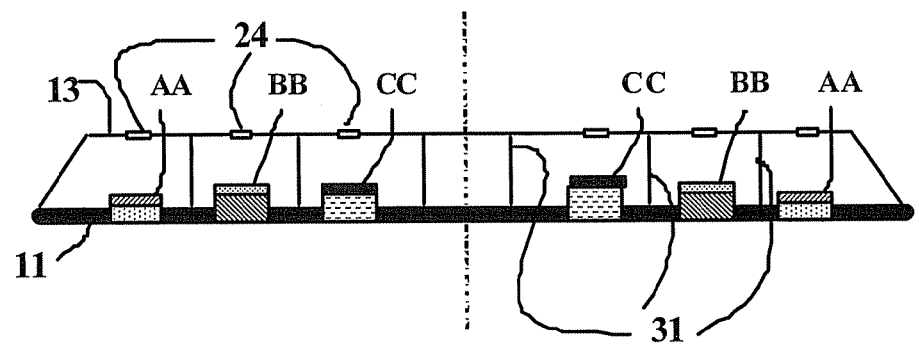
FIG. 5G is a cross section side view of a patch implemented as concentric rings having different emissivity, conductivity, and thicknesses in accordance with a first preferred embodiment of the present invention.

FIG. 5F is a top view and FIG. 5G is a side view cross section of an implementation of contact component 11 similar to that of FIG. 5D and FIG. 5E but where sections AA, BB, and CC are implemented as concentric rings.

Figure 6:
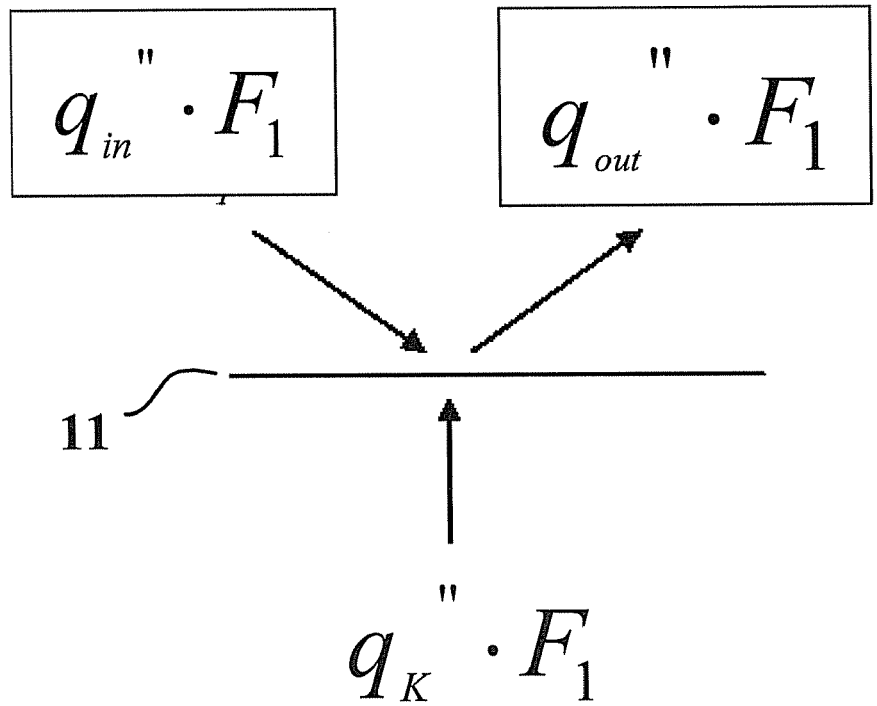
FIG. 6 is a diagram of heat flux balance.

The measurement of the heat flux is now described with reference to FIG. 6. Note: The direction of heat flow between contact component 11 and the skin is from the higher temperature to the lower. It is assumed for the sake of description that contact component 11 is cooler and therefore the flow is from the skin to the component. This is also shown in FIG. 6.

We can ignore convection from contact component 11 to the environment as this is minimized by insulating cover 13. Since contact component 11 is in a thermal steady state, the energy balance on its surface is such that the total amount of heat coming into the component equals the amount going out. Therefore, either:

$(q''_k \cdot F_1) + (q''_{in} \cdot F_1) - (q''_{out} \cdot F_1) = 0$: (when contact component 11 is in a thermal steady state (thermal equilibrium)

or:

$$(q''_{out} \cdot F_1) - (q''_{in} \cdot F_1) = q''_k \cdot F_1 \quad (1)$$

where:

$F_1$ is the area of the contact component 11 surface and where:

$q''_k \cdot F_1$ is the incoming heat energy per time unit from the skin surface to the contact component 11 via conductivity.

$q_{in}'' \cdot F_1$ is the incoming heat energy per time unit radiated back to contact component 11 from the inside of cover 13.

$q_{out}'' \cdot F_1$—is the outgoing heat energy per time unit radiated by contact component 11 Dividing equation (1) by $F_1$ and defining the difference between the incoming and outgoing radiation as Δq we get:

$$\Delta q = q_{out}'' - q_{in}'' = q_k'' \quad (2)$$

For a steady state and omitting convection losses, by the definition of heat flux we derive:

$$q''_K = K \cdot \frac{\Delta T}{\Delta X} = \left(\frac{K_{eff}}{\Delta X}\right)(Tdeep - Tsurface). \quad (3)$$

However, from the radiation equations for the case of two co-radiating surfaces, it can easily be proven that $\Delta q$, in our case is given by:

$$\Delta q = q''_{out} - q''_{in} = \frac{\sigma T_1^4 - \sigma T_2^4}{\frac{1-\varepsilon_1}{\varepsilon_1} - \frac{1-\varepsilon_2}{\varepsilon_2}(F_1/F_1) + 1} \quad (4)$$

or, by substituting in equation (2)

$$q''_K = \frac{\sigma T_1^4 - \sigma T_2^4}{\frac{1-\varepsilon_1}{\varepsilon_1} - \frac{1-\varepsilon_2}{\varepsilon_2}(F_1/F_1) + 1}$$

where
$\sigma$ is the Stephan Bolzman constant
$T_2$ is the temperature of insulating cover 13, which can be measured directly. $T_1$ is the temperature of the surface of contact component 11 at point 1, which is measured indirectly by radiometer reader 12. Using $T_1$ and $T_1$ in equation (4), the (incoming) conductive heat flow ($q_k''$) at contact component surface point 1 can be calculated. It should be noted here that $q_k''$ is equal to $q_s''$ as they both are representing the heat flux on the contact component surface. Thus, one can substitute $q_k''$ in equation (3) instead of $q_s''$.

In equation (3), we have $$\left(\frac{K_{eff}}{\Delta X}\right)$$

and Tdeep as unknowns. Based on (3) we can have:

$$[q''_k] \cdot \left(\frac{\Delta X}{K_{eff}}\right) - Tdeep = -Tsurface$$

Tsurface is $T_1$. Both Tsurface and $q_k''$ are derived from measurements, There are various techniques for solving for the remaining two unknowns $$\left(\left(\frac{K}{\Delta X}\right)_{eff}\right)$$

and Tdeep). As the model is based on the assumption that the medium as well as the patch are in thermal steady state, it is imperative to determine whether they are in thermal steady state or not before deriving the values of $$\left(\frac{K}{\Delta X}\right)_{eff}$$

and Tdeep. Thermal steady state is characterized by constant heat flux. One can use repeated measurements to obtain a series of $q_k''$ values and once the changes are within a predetermined acceptable range, say 1% of the value, one can determine that the thermal steady state condition has occurred.

One technique is the Least Square method. For two unknowns, at least three equations are required. The values for the three equations are retrieved by making three different measurements at spots AA, BB, and CC, each spot having unique thermal boundary conditions, which create a unique surface temperature at that spot. The thermal boundary conditions refer to different conductivity, thickness, emissivity, or a combination of them. Repeating equation (3) for each spot yields a system of linear equations.

We define unknown vector $$\hat{X} \triangleq \begin{pmatrix} \left(\frac{\Delta X}{K}\right)_{eff} \\ Tdeep \end{pmatrix}$$

and matrix $$A \triangleq \begin{bmatrix} q''k_{AA} & -1 \\ q''k_{BB} & -1 \\ q''k_{CC} & -1 \end{bmatrix}$$

Where $\hat{b}$ is defined as:

$$\hat{b} = \begin{pmatrix} -Tsurface_{AA} \\ -Tsurface_{BB} \\ -Tsurface_{CC} \end{pmatrix}$$

the vector of temperature surface measurements at three points.

We can rewrite (3) in the following way:

$$A \cdot \hat{X} = \hat{b} \quad (5)$$

Dimension (3*2) (2*1) (3*1)

where A is the "model" matrix, $\hat{X}$ is the unknown vector for estimation, and $\hat{b}$ is the vector of the measurements.

As mentioned, to make the three surface measurements spots, three areas (AA, BB, CC) are provided on contact component 11 of patch 10, each having different boundary conditions and each substantially thermally insulated from the others. FIG. 5A illustrates a sample implementation of such an embodiment of patch 10, wherein the patch is divided into areas AA, BB, and CC with different emissivities, each location with its own cover 13. Alternatively, a single cover could be used with dividers insulating each location from the others. In addition to the surface measurements, a measurement $T_2$ is made on at least one of covers 13.

If the emissivity is differentiated enough in each area, we will measure three different surface temperatures (Tsurface$_{AA,BB,CC}$) as well as three different incoming conducted heat flows (q''$k_{AA, BB,CC}$) from which one can derive the internal temperature (Tdeep) and the effective thermal resistivity $$\left(\left(\frac{K_{\text{eff}}}{\Delta X}\right)\right)$$

between the interior and the surface. Note: Due to inaccuracies associated with the measurements and the one dimensional model, the accuracy of the values of Tdeep and $$\left(\frac{K_{\text{eff}}}{\Delta X}\right)$$

can be further improved by correcting these values using a predetermined correction table, equation based on empirical data, or more complicated models.

(Note that $T_{e_{AA,BB,CC}}$ is used to derive $T_{1_{AA,BB,CC}}$ according to equation (7) (described later) while $T_{2_{AA,BB,CC}}$ which is measured directly.)

Radiometer 12 is used to read the effective surface temperature $T_e$ of contact component 11 at point 1 in each of areas AA, BB, and CC, and it is used to read temperature $T_2$ of cover 13 at point 2.

The calibration of radiometer 12 is now described. In calibration versus black body, for every temperature the output power measured on the radiometer's sensor, that is:

$$P\left(\frac{waii}{\text{cm}^2}\right) = \Pi \frac{d_o^2}{4} \omega \tau_o \cdot \sigma Te^4$$

where:
$d_o$=Diameter of sensor.
$\omega$=The sensor's spatial angle.
$\tau_o$=Transmissivity of IR-read access point 24.
$\sigma$=Stephan Bolzman constant
$T_e$=Effective temperature of a black body In our case, where power resulting from radiation into the radiometer is measured:

$$\underbrace{\Pi \frac{d_o^2}{4} \omega \tau_o}_{K} (\varepsilon_{1J} T_1^4 + \rho \varepsilon_{2J} T_2^4) = K \cdot T_e^4 \quad (6)$$

That is, the temperature measured in the radiometer is a combination of $T_1$ and $T_2$.

We can simplify and write that:

$$T_e^4 = \varepsilon_{1J} T_1^4 + \rho \varepsilon_{2J} T_2^4$$

And if we substitute the $\varepsilon_{2J}$ and $\varepsilon_{1J}$ terms, we get:

$$T_e^4 = \frac{T_1^4 \left[\varepsilon_1 \varepsilon_2 + \frac{F_1}{F_2} \rho_2 \varepsilon_1\right] + T_2^4 \rho_1 \varepsilon_2}{\varepsilon_2 + \frac{F_1}{F_2} \varepsilon_1 \rho_2} \quad (7)$$

This equation links the temperature $T_e$ that reader 12 detects at point 1 on contact component 11 and the temperature $T_2$ that reader 12 detects at point 2 on the surface of insulating cover 13.

Therefore, once we have values $\varepsilon_1$, $\varepsilon_2$, $F_1$, $F_2$, $\rho_2$ and $T_2$ defined, we can easily derive value $T_1$ from the radiometer's reading $T_e$ at location 1.

Figure 7:
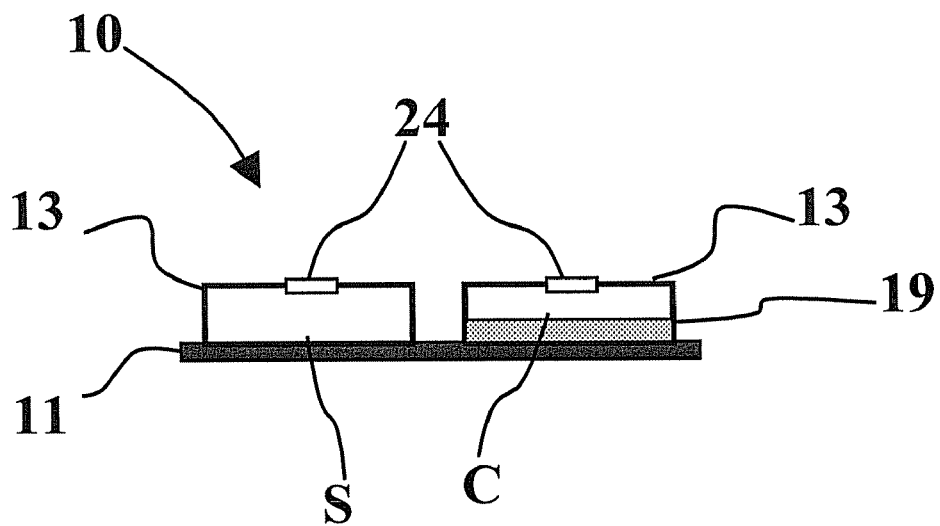
FIG. 7 is a cross section side view of a contact component in accordance with a second preferred embodiment of the present invention.

A second embodiment of the present invention is now described with reference to FIG. 7, which is a cross-sectional view of patch 10 in this embodiment.

Whereas, in the first embodiment $T_1$ (surface temperature) and $q''_k$ are derived using equation (4), in the second embodiment described here, parameter $q''_k$ is measured by direct measurement of the temperature difference between two points on the surface of contact component 11.

In this embodiment, contact component 11 comprises different measurement spots having different thermal boundary conditions determined by different thermal conductivity, and/or different thickness. For example, in FIG. 7, spot S is directly on contact component 11 while spot C is on top of a layer of insulation 19.

Each spot (S and C) is covered by a cover 13 as was described earlier. Temperatures at spots S and C are read by reader 12, which can be any of various implementations (for example radiometer, transducer signal reader, or other spot thermal magnitude reader) as was mentioned earlier.

In spot S, the radiometer directly measures the steady state temperature of the contact surface, defined as $T_S$. In spot C, the radiometer measures temperature $T_C$ on top of insulation member 19, which is lower than $T_S$.

The heat flux on top of insulation 19 (spot C) is given by:

$$q''_s = \frac{K_s}{\Delta X_s}(T_S - T_C)$$

with the assumption that there are no lateral effects due to spatial heat flow.

Thus, from the temperature difference between spots (S and C) on contact component 11 a magnitude can be derived that is linearly related to the heat flux. To prevent lateral effects, contact component 11 has to be large relative to the distance between spot S and spot C.

Since in a steady state all the heat fluxes throughout the layers are constant, one can write:

$$q^* = \underbrace{\frac{K_s}{\Delta X_s}(T_S - T_C)}_{\Delta T} = \left(\frac{K_{\text{eff}}}{\Delta X}\right)(Tdeep - T_S) \quad (8)$$

From here we get:

$$\Delta T \left(\frac{K_s}{\Delta X_s} \cdot \frac{\Delta X}{K_{\text{eff}}}\right) - Tdeep = -T_S$$

In order to solve the equation, we will note that the unknowns here are:

$$\left(\frac{K}{\Delta X}\right)_s \cdot \left(\frac{\Delta X}{K_{\text{eff}}}\right)$$

and Tdeep
It should be noted that $$\left(\frac{K}{\Delta X}\right)_s$$

can be measured directly or calibrated during manufacture of patch 10, however as this parameter is a multiplying the $$\left(\frac{\Delta X}{K_{eff}}\right)$$

term, one can refer to the multiplication $$\left(\frac{K}{\Delta X}\right)_s \cdot \left(\frac{\Delta X}{K_{eff}}\right)$$

as an unknown, unless the explicit value $$\left(\frac{\Delta X}{K_{eff}}\right)$$

is required. In such a case, after obtaining the unknown $$\left(\frac{K}{\Delta X}\right)_s \cdot \left(\frac{\Delta X}{K_{eff}}\right),$$

one can divide it by the calibrated value of $$\left(\frac{K}{\Delta X}\right)_s$$

to get.

$$\left(\frac{\Delta X}{K_{eff}}\right)$$

To find two unknowns by means of a least square, three measurements pairs are required, and therefore we will define in this configuration three measuring locations, each with a pair of measurement spots $s_i$ where we will measure values of $Ts_i$ and $c_i$ where we will measure values of $Tc_i$ where the index i indicates the measurement location. Thus, in the case where we use three locations, we will get the following pairs of measurements: $Ts_1$, $Tc_1$ at the first location, $Ts_2$, $Tc_2$ at the second location and $Ts_3$, $Tc_3$ at the third location. All of these spots will have different thermal boundary conditions, as for example, by having different insulation (19a, 19b, 19c). Next to each spot $c_i$ is a spot $s_i$, located close enough to the $c_i$ spot that their separation distance is substantially smaller than the distance separating adjacent measurement locations. As will be shown later, the difference between each pair of temperatures $Ts_1$, $Tc_1$ is used to calculate the one dimensional heat flux from the internal region towards the external surface. Normally, the two spots have to be located on the same axis along which the heat flux is measured. On the other hand, in the case of using radiometer as the reading device, it is imperative to get a line of sight to both of the spots at the same time. For this reason the two spots are located one beside the other. To enable the radiometer measurement, but still to get a valid measurement of the heat flux along the same axis, we minimize the distance between spots $s_i$ and $c_i$, and therefore the one dimensional assumption remains valid.

Note: In the case where contact component 11 has high conductivity, Ts1~Ts2~Ts3, so it is enough to measure one Ts value.

Figure 8A:
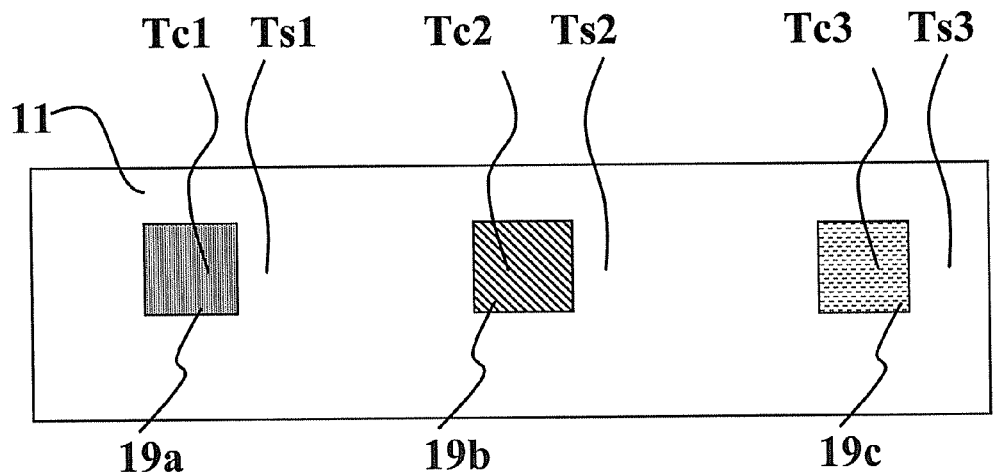
FIG. 8A is a top view of a contact component in accordance with a second preferred embodiment of the present invention.
Figure 8B:
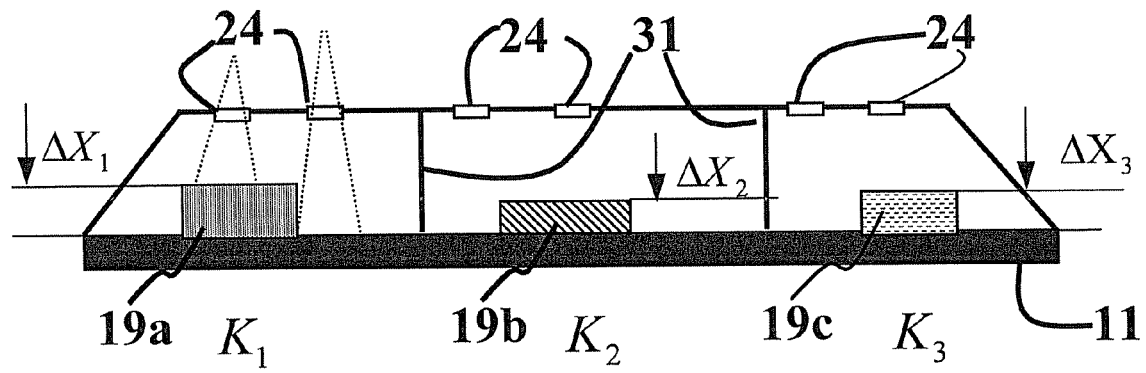
FIG. 8B is a cross section side view of a second preferred embodiment of the present invention.

This configuration of contact component 11 is shown in top view in FIG. 8A and in side view in FIG. 8B.

In the case of using heat or temperature transducers in the patch, each pair of transducers that are located in one location should be located one above the other with an insulation member 26 between them, as is shown in FIG. 3B for one location. This configuration is done per measurement location thus, in the case of three measurement locations, there will be three pairs of heat or temperature transducers and three insulation members.

It should be noted that $\Delta Xs$ and $Ks$ can be identical in some or all of the measurement locations as long as the following relationship is maintained:

$$\left(\frac{\Delta X}{K_s}\right)_i \neq \left(\frac{\Delta X}{K_s}\right)_j, \left(\frac{K_s}{\Delta X}\right)_i \neq \left(\frac{K_s}{\Delta X}\right)_j$$

$i, j = 1 \ldots 3 \ j \neq i$

Since there are three points of measurement, we will receive three separate measurements for $Ts_i$ and $Tc_i$, which will define three separate $\Delta T_i$. In vector format we will be able to write:

$$\underbrace{\begin{bmatrix} \Delta T_1 \cdot \frac{Ks_1}{\Delta X_1} - 1 \\ \Delta T_2 \cdot \frac{Ks_2}{\Delta X_2} - 1 \\ \Delta T_3 \cdot \frac{Ks_3}{\Delta X_3} - 1 \end{bmatrix}}_{A} \times \underbrace{\begin{bmatrix} \left(\frac{\Delta X}{K_{eff}}\right) \\ \\ Tdeep \end{bmatrix}}_{\hat{X}} = \underbrace{\begin{bmatrix} Tc_1 \\ Tc_2 \\ Tc_3 \end{bmatrix}}_{\hat{b}}$$

Dimensions: 3×2 2×1 3×1
which can be written: $A \cdot \hat{X} = \hat{b}$

This principle can be implemented for three or more locations.

Figure 9:
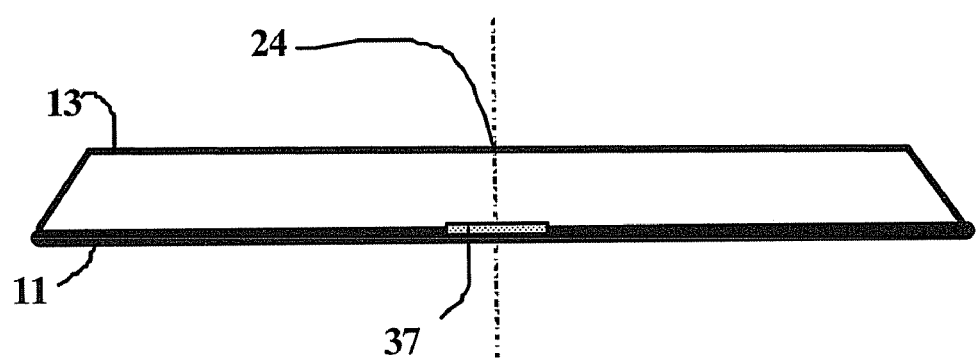
FIG. 9 is a cross section side view of a contact component in accordance with a third preferred embodiment of the present invention.

A third embodiment of the present invention is now described with reference to FIG. 9, which is a cross section side view of patch 10. In this configuration we assume that $q_s'' \approx 0$ and no radiation or convection effects occur on the surface. In this case, if the contact component 11 is big enough to avoid lateral heat flux and the cover 13 emissivity is low on both its internal and external surface (for example with a reflective surface) and if access element 24 does not leak a significant amount of radiation (for example a small opening having an area of less than 5% of the total area of the cover), then we can assume that Ts is close enough to Tdeep to be considered equivalent. Therefore, a direct measurement of Ts can be used to find Tdeep. For example, in the case of human body temperature measurement, a patch could have a diameter larger than 20 mm and a cover 13 having emissivity of less than 0.1 on both surfaces of the cover.

In order to get good signal to noise ratio, one can use a high emissivity surface 37 for reading, for example 0.8-0.9. In order to determine whether the medium and the patch are in a thermal steady state, it is imperative to perform a series of measurements of Ts. Once the change of these value is lower than a predetermined acceptable limit, say for example less than 1%, the condition of thermal steady state is fulfilled and the value of Tdeep can be obtained.

In summary, the present invention provides a fast noninvasive means for determining the internal temperature of an object. It has been explained with reference to a body temperature implementation and can equally be applied for other animate objects as well as inanimate objects.

It should be clear that the description of the embodiments and attached Figures set forth in this specification serves only for a better understanding of the invention, without limiting its scope as covered by the following Claims.

It should also be clear that a person skilled in the art, after reading the present specification could make adjustments or amendments to the attached Figures and above described embodiments that would still be covered by the following Claims.

The invention claimed is:

1. A temperature measurement device for a non-invasive measurement of the internal temperature of a physical body or thermal resistivity, the body comprising a thermally conductive medium between an internal region with a substantially constant internal temperature and an external surface with a surface temperature, the device comprising:
    a patch for attachment to an external surface of a body having an internal temperature, the patch comprising:
        at least three contact components, which are configured to contact the external surface of the body at different, respective measurement locations and to have at least three different thermal boundary conditions; and
        an insulating cover for thermally insulating said at least three contact components from ambient thermal conditions;
    a reader for acquiring at least three respective thermal magnitudes from the said at least three contact components; and
    a processing unit for processing said at least three respective thermal magnitudes in order to derive the internal temperature of the body.

2. The device of claim 1, wherein gas is provided between the insulating cover and the at least three contact components.

3. The device of claim 2, wherein the gas is transparent to infra-red radiation.

4. The device of claim 3, wherein the gas is air.

5. The device of claim 1, wherein a vacuum is provided between the insulating cover and the at least three contact components.

6. The device of claim 1, wherein the measurement locations are characterized as having distinct properties selected from the group of properties consisting of: different thermal conductivity, different thickness, or different emissivity.

7. The device of claim 1, wherein said measurement locations are characterized in that each measurement location facilitates two or more measurement spots facilitating different thermal boundary conditions on the external surface.

8. The device of claim 7, wherein the different thermal boundary conditions are characterized as having distinct properties selected from the group of properties comprising: different thermal conductivity or different thickness.

9. The device of claim 7, wherein the measurement locations are separated by thermal insulation.

10. The device of claim 7, wherein said two or more measurement spots are separated by a distance that is substantially smaller than the distance separating adjacent measurement locations.

11. The device of claim 1, wherein the patch is provided with at least one pair of thermally separated heat or temperature transducers for each measurement location, each transducer provided with leads to terminals external to the patch, which the reader can contact for reading.

12. The device of claim 1, wherein the reader is an infra-red radiation radiometer.

13. The device of claim 12, wherein the insulating cover is provided with a point of access through which the radiometer can acquire one or more thermal magnitudes on the patch.

14. The device of claim 13, wherein the point of access is selected from the group consisting of: a window, an opening, a diaphragm, or a shutter.

15. The device of claim 1, wherein each of the at least three contact components comprises one location of substantially low thermal resistivity and substantially low emissivity, the cover has low emissivity, and wherein the cover is large enough to avoid lateral heat flux, thereby allowing at a thermal steady state the temperature on each of the at least one contact components to be substantially equal to the internal temperature.

16. The device of claim 1, further comprising a user interface for enabling a user to calibrate and operate the reader and to be informed of the calculated internal temperature.

17. The device of claim 1, wherein the patch further comprises identification information about the physical body, the reader further comprises means for reading identification information.

18. The device of claim 17, wherein the means for reading the identification information is a bar code reader.

* * * * *